United States Patent [19]
Goldie et al.

[11] Patent Number: 4,834,984
[45] Date of Patent: May 30, 1989

[54] CONTROLLED RELEASE DIHYDROCODEINE COMPOSITION

[75] Inventors: Robert S. Goldie; Sandra T. A. Malkowska; Stewart T. Leslie, all of Cambridge, England; Ronald B. Miller, Basel, Switzerland

[73] Assignee: Euroceltique S.A., Luxembourg, Luxembourg

[21] Appl. No.: 52,584

[22] Filed: May 19, 1987

[30] Foreign Application Priority Data

Jun. 10, 1986 [GB] United Kingdom ................ 8614153
Sep. 2, 1986 [GB] United Kingdom ................ 8621206

[51] Int. Cl.$^4$ ................................ A61K 9/14
[52] U.S. Cl. .................... 424/488; 424/457; 424/468; 424/469; 424/484; 424/499; 424/502
[58] Field of Search ............ 424/484, 498, 502, 485, 424/488, 457, 468, 469, 499

[56] References Cited

U.S. PATENT DOCUMENTS 4,629,620 12/1986 Lindahl et al. ................ 424/467 X

FOREIGN PATENT DOCUMENTS 0821790 10/1959 United Kingdom ................ 424/498
0935426 8/1963 United Kingdom ................ 424/498
1125882 9/1968 United Kingdom ................ 424/498

Primary Examiner—Thurman K. Page
Attorney, Agent, or Firm—Steinberg & Raskin

[57] ABSTRACT

A solid controlled release, oral dosage form, the dosage form comprising an analgesically effective amount of dihydrocodeine or a salt thereof in a controlled release matrix wherein the dissolution rate in vitro of the dosage form, when measured by the USP Paddle Method at 100 rpm in 900 ml aqueous buffer (pH between 1.6 and 7.2) at 37° C. is between 25% and 60% (by weight) dihydrocodeine released after 1 hour, between 45% and 80% (by weight) dihydrocodeine released after 2 hours, between 60% and 90% (by weight) dihydrocodeine released after 3 hours and between 70% and 100% (by weight) dihydrocodeine released after 4 hours, the in vitro release rate being independent of pH between pH 1.6 and 7.2 and chosen such that the peak plasma level of dihydrocodeine obtained in vivo occurs between 2 and 4 hours after administration of the dosage form.

19 Claims, No Drawings

CONTROLLED RELEASE DIHYDROCODEINE COMPOSITION

The present invention relates to a solid, controlled release, oral dosage form containing dihydrocodeine for use in the treatment of moderate to severe pain.

According to the present invention there is provided a solid, controlled release, oral dosage form, the dosage form comprising an analgesically effective amount of dihydrocodeine or a salt thereof in a controlled release matrix wherein the dissolution rate in vitro of the dosage form, when measured by the USP Paddle Method at 100 rpm in 900 ml. aqueous buffer (pH between 1.6 and 7.2) at 37° C. is between 25% and 60% (by wt) dihydrocodeine released after 1 hour, between 45% and 80% (by wt) dihydrocodeine released after 2 hours, between 60% and 90% (by wt) dihydrocodeine released after 3 hours and between 70% and 100% (by wt) dihydrocodeine released after 4 hours, the in vitro release rate being independent of pH between pH 1.6 and 7.2 and such that the peak plasma level of dihydrocodeine obtained in vivo occurs between 2 and 4 hours after administration of the dosage form.

USP Paddle Method is the Paddle Method described in US Pharmacopoeia XXI (1985).

In the present specification, "independent of pH" means that the difference, at any given time, between the amount of dihydrocodeine (or a salt) released at pH 1.6 and the amount released at any other pH upto, and including, pH 7.2 (when measured in vitro using the USP Paddle Method at 100 rpm in 900 ml aqueous buffer) is 5% (by weight) or less. The amounts released being, in all cases, a mean of at least three experiments.

In the present specification, "peak plasma level of dihydrocodeine obtained in vivo" refers to the maximum mean concentration of dihydrocodeine found in the plasma of at least six healthy human volunteers, when (the volunteers are) subjected to a single dose, pharmacokinetic study.

Preferably the dissolution rate is between 25% and 50% (by wt) dihydrocodeine released after 1 hour, between 45% and 70% after 2 hours between 60% and 80% after 3 hours and between 70% and 90% after 4 hours.

Most preferably, the dissolution rate is between 30% and 50% (by wt) dihydrocodeine released after 1 hour, between 45% and 65% after 2 hours, between 60% and 75% after 3 hours and between 70% and 85% after 4 hours.

Preferably the peak plasma level of dihydrocodeine is obtained in vivo between 2.25 and 3.75 hours after administration of the dosage form.

When the dihydrocodeine is administered as dihydrocodeine tartrate and the method of dihydrocodeine in plasma analysis is
(i) Extraction from plasma into dichloromethane,
(ii) Extraction from dichloromethane into dilute sulphuric acid, and
(iii) HPLC,
the peak plasma level of dihydrocodeine (per ml. of plasma) is preferably between $1.5 \times 10^{-6}$, most preferably between $2 \times 10^{-6}$ and $3 \times 10^{-6}$, of the amount of dihydrocodeine tartrate administered orally.

Thus, if 60 mg of dihydrocodeine tartrate is administered, the peak plasma level of dihydrocodeine is preferably between 90 and 180 ngml$^{-1}$, especially between 120 and 180 ngml$^{-1}$.

When dihydrocodeine base or a salt other than the tartrate is administered, the preferred ratio of drug administered to peak plasma level of dihydrocodeine must be adjusted according to the molecular weight of the base or salt. By keeping within these narrow ranges for in vitro dissolution rates, the present inventors have surprisingly found that although the present oral dosage forms give peak plasma levels of dihydrocodeine between 2 and 4 hours after administration, they still afford therapeutic levels of dihydrocodeine in vivo over at least a 12 hour period, and can therefore be used on a twice daily basis.

In order to obtain a controlled release drug dosage form having at least a 12 hour therapeutic effect, it is usual in the pharmaceutical art to produce a formulation that gives a peak plasma level of the drug between about 4–8 hours after administration (in a single dose study). The present inventors have surprisingly found that, in the case of dihydrocodeine, a peak plasma level at between 2–4 hours after administration gives at least 12 hours pain relief.

Most surprisingly, the present inventors have also found that the pain relief obtained with the present formulation is greater than that achieved with normal release formulations giving peak plasma levels (of dihydrocodeine) in the normal period of 1-2 hours after administration.

Furthermore, in the case of the present dosage form, therapeutic levels are generally achieved without concurrent side effects, such as nausea, vomiting, constipation and drowsiness, which are often associated with high blood levels of dihydrocodeine. There is also evidence to suggest that the use of the present dosage forms leads to a reduced risk of drug addiction.

A further advantage of the present composition, which releases dihydrocodeine at a rate that is independent of pH between 1.6 and 7.2, is that it avoids dose dumping upon oral administration. In other words, the dihydrocodeine is released evenly throughout the gastrointestinal tract.

The present oral dosage form may be presented as, for example, granules or pellets in a capsule or in any other suitable solid form. Preferably, however, the oral dosage form is a tablet.

The present oral dosage form preferably contains between 30 and 180 mg, especially between 60 and 120 mg, of dihydrocodeine tartrate. Alternatively the dosage form may contain mole equivalent amounts of other dihydrocodeine salts or of the dihydrocodeine base.

The present controlled release matrix may be any matrix that affords in vitro dissolution rates of dihydrocodeine within the narrow ranges required and that releases the dihydrocodeine in a pH independent manner.

Suitable materials for inclusion in the controlled release matrix are
(a) Hydrophilic or hydrophobic polymers, such as gums, cellulose ethers and protein derived materials. Of these polymers, the cellulose ethers, especially hydroxyalkylcelluloses and carboxyalkylcelluloses, are preferred. The oral dosage form may contain between 1% and 80% (by weight) of at least one hydrophilic or hydrophobic polymer.
(b) Digestible, long chain ($C_8$–$C_{50}$, especially $C_8$–$C_{40}$), substituted or unsubstituted hydrocarbons, such as fatty acids, fatty alcohols, glyceryl esters of fatty acids, mineral oils and waxes. Hydrocarbons having a melting point of between 25° and 90° C. are preferred.

Of these long chain hydrocarbon materials, fatty (aliphatic) alcohols are preferred. The oral dosage form may contain up to 60% (by weight) of at least one digetible, long chain hydrocarbon.

(c) Polyalkylene glycols. The oral dosage form may contain up to 60% (by weight) of at least one polyalkylene glycol.

One particularly suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol.

The at least one hydroxyalkyl cellulose is preferably a hydroxy ($C_1$ to $C_6$) alkyl cellulose, such as hydroxypropylcellulose, hydroxypropylmethylcellulose and especially hydroxyethyl cellulose. The amount of the at least one hydroxyalkyl cellulose in the present oral dosage form will be determined inter alia, by the precise rate of dihydrocodeine release required. Preferably however, the oral dosage form contains between 2% and 20%, especially between 3% and 12% (by wt) of the at least one hydroxyalkyl cellulose.

The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of dihydrocodeine release required. It will also depend on whether at least one polyalkylene glycol is present in or absent from the oral dosage form. In the absence of at least one polyalkylene glycol, the oral dosage form preferably contains between 8% and 40%, especially between 12% and 36% (by wt) of the at least one aliphatic alcohol. When at least one polyalkylene glycol is present in the oral dosage form, then the combined weight of the at least one aliphatic alcohol and the at least one polyalkylene glycol preferably constitutes between 8% and 40%, especially between 12% and 36% (by wt) of the total dosage form.

In the present preferred dosage form, the ratio of the at least one hydroxyalkyl cellulose to the at least one aliphatic alcohol/polyalkylene glycol determines, to a considerable extent, the release rate of the dihydrocodeine from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferably between 1000 and 15,000 especially between 1500 and 12,000.

In addition to the above ingredients, the controlled release matrix may also contain suitable quantities of other materials, e.g. diluents, lubricants, binders, granulating aids, colorants, flavorants and glidants that are conventional in the pharmaceutical art.

In order to facilitate the preparation of a solid, controlled release, oral dosage form according to this invention there is provided, in a further aspect of the present invention, a process for the preparation of a solid, controlled release, oral dosage form according to the present invention comprising incorporating dihydrocodeine or a salt thereof in a controlled release matrix. Incorporation in the matrix may be effected, for example, by (a) wet granulating at least one water soluble hydroxyalkyl cellulose with dihydrocodeine or a dihydrocodeine salt to form granules, (b) mixing the hydroxyalkyl cellulose containing granules with at least one $C_{12}$-$C_{36}$ aliphatic alcohol, and (c) optionally, compressing and shaping the granules.

In this case the amount of water added during the wet granulation step is preferably between 1.5 and 5 times, especially between 1.75 and 3.5 times, the dry weight of the hydroxyalkylcellulose.

The present solid, controlled release, oral dosage form and processes for its preparation will now be described by way of example only.

EXAMPLE 1

Dihydrocodeine tartrate (60 gm) was wet granulated with anhydrous lactose (58.4 gm) and hydroxyethyl cellulose (20.4 gm; Natrosol 250 HX, Trade Mark) for 10 minutes and the granules were sieved through a 16 mesh screen. The granules were then dried in a Fluid Bed Dryer at 60° C.

To the warmed dihydrocodeine containing granules was added molten cetostearyl alcohol (62.2 gm) and the whole was mixed thoroughly. The mixture was allowed to cool in the air, regranulated and sieved through a 16 mesh screen.

Talc (2.0 gm) and magnesium stearate (2.0 gm) were then added and mixed with the granules. The granules were then compressed into 1000 tablets each containing,

|  | mg/tablet |
| --- | --- |
| Dihydrocodeine Tartrate | 60.0 |
| Anhydrous Lactose | 58.4 |
| Hydroxyethylcellulose | 20.4 |
| Cetostearyl alcohol | 62.2 |
| Talc | 2.0 |
| Magnesium stearate | 2.0 |

EXAMPLE 2

The procedure of Example 1 was followed except that the quantities of the ingredients were chosen to give 1000 tablets each containing,

|  | mg/tablet |
| --- | --- |
| Dihydrocodeine Tartrate | 120.0 |
| Anhydrous Lactose | 94.0 |
| Hydroxyethylcellulose | 20.0 |
| Cetostearyl alcohol | 60.0 |
| Talc | 3.0 |
| Magnesium stearate | 3.0 |

EXAMPLE 3

The procedure of Example 1 was followed except that the quantities of the ingredients were chosen to give 1000 tablets each containing,

|  | mg/tablet |
| --- | --- |
| Dihydrocodeine Tartrate | 90.0 |
| Anhydrous Lactose | 40.5 |
| Hydroxyethylcellulose | 22.5 |
| Cetostearyl Alcohol | 67.5 |
| Talc | 4.5 |

|  | mg/tablet |
| --- | --- |
| Magnesium Stearate | 3.75 |

EXAMPLE 4

The procedure of Example 1 was followed except that the quantities of the ingredients were chosen to give 1000 tablets each containing,

|  | mg/tablet |
| --- | --- |
| Dihydrocodeine Tartrate | 120.0 |
| Anhydrous Lactose | 54.0 |
| Hydroxyethylcellulose | 30.0 |
| Cetostearyl Alcohol | 90.0 |
| Talc | 6.0 |
| Magnesium Stearate | 5.0 |

EXAMPLE 5

The procedure of Example 1 was repeated except that the wet granulation step proceeded for 12 minutes.

EXAMPLE 6

The procedure of Example 1 was repeated except that the wet granulation step proceeded for 16 minutes.

In Vitro Dissolution Studies

A. In vitro dissolution studies were conducted on tablets prepared as described in Example 1. The dissolution method was the USP Paddle Method described in US Pharmacopoeia XXI (1985). The paddle speed was 100 rpm, the temperature was 37° C. and the solution was
(a) 900 ml. aqueous buffer (pH 1.6)
(b) 900 ml. aqueous buffer (pH 4.6)
(c) 900 ml. aqueous buffer (pH 6.5, USP buffer), and
(d) 900 ml. aqueous buffer (pH 7.2).

The amount of dihydrocodeine tartrate released was analysed by uv spectrophotometry (at 284 nm).
Results are given in Table 1.

TABLE 1

| Time (hr) | wt. % Dihydrocodeine Tartrate released | | | |
| --- | --- | --- | --- | --- |
|  | pH 1.6 | pH 4.6 | pH 6.5 | pH 7.2 |
| 1 | 43.8 | 43.6 | 43.9 | 44.1 |
| 2 | 63.4 | 62.1 | 62.5 | 63.1 |
| 3 | 76.7 | 75.1 | 75.4 | 77.6 |
| 4 | 86.3 | 85.0 | 84.8 | 87.4 |
| 5 | 92.1 | 91.3 | 91.5 | 93.8 |
| 6 | 94.9 | 94.6 | 94.9 | 97.6 |
| 7 | 95.9 | 96.3 | 96.3 | 99.7 |
| 8 | 96.0 | 96.7 | 97.5 | 100.0 |
| 9 | 96.3 | 97.0 | 98.2 | 100.5 |
| 10 | 96.3 | 97.0 | 98.9 | 100.6 |

B. Similar in vitro studies were conducted on tablets prepared as described in Example 3, but using 900 ml aqueous buffer (pH 6.5, USP buffer) only.
Results are given in Table 2.

TABLE 2

| Time (hr) | Wt. % Dihydrocodeine Tartrate released |
| --- | --- |
| 1 | 38.6 |
| 2 | 55.8 |
| 3 | 68.5 |
| 4 | 78.7 |
| 5 | 86.5 |
| 6 | 92.6 |
| 7 | 96.7 |
| 8 | 99.2 |

C. Similar in vitro studies were conducted on tablets prepared as described in Example 4, but using 900 ml aqueous buffer (pH 6.5, USP buffer) only.
Results are given in Table 3.

TABLE 3

| Time (hr) | Wt. % Dihydrocodeine Tartrate released |
| --- | --- |
| 1 | 31.9 |
| 2 | 48.6 |
| 3 | 60.9 |
| 4 | 70.9 |

D. Similar in vitro studies were conducted on tablets prepared as described in Example 5, but using 900 ml aqueous buffer (pH 6.5, USP buffer) only.
Results are given in Table 4.

TABLE 4

| Time (hr) | Wt. % Dihydrocodeine Tartrate released |
| --- | --- |
| 1 | 42.1 |
| 2 | 60.6 |
| 3 | 73.6 |
| 4 | 83.7 |
| 5 | 91.2 |
| 6 | 96.5 |
| 7 | 99.3 |

Clinical Studies

A. A single dose, randomised, comparative, pharmacokinetic study was conducted on 6 subjects employing,
(i) A controlled release dihydrocodeine tartrate tablet prepared as described in Example 1, (a 60 mg dose), and
(ii) 2×30 mg Dihydrocodeine tartrate tablets (DF118; Trade Mark; a 60 mg dose).

Analysis of the plasma samples for dihydrocodeine was performed as follows:
(a) Extraction of the plasma sample with dichloromethane,
(b) Extraction of the dichloromethane layer with dilute sulphuric acid, and
(c) HPLC analysis of the acidic layer.
Results are given in Table 5.

TABLE 5

| Time (hr) | Mean Plasma Conc. (ng/ml$^{-1}$) | |
| --- | --- | --- |
|  | Example 1 | DF118 |
| 0.25 | — | 7 |
| 0.50 | — | 80 |
| 0.75 | — | 160 |
| 1.0 | 62 | 205 |
| 1.25 | — | 177 |
| 1.50 | — | 194 |
| 2.0 | 108 | 183 |
| 3.0 | 130 | 137 |
| 4.0 | 111 | 119 |
| 5.0 | 114 | — |
| 6.0 | 110 | 73 |
| 8.0 | 85 | 51 |
| 10.0 | 63 | 31 |
| 12.0 | 34 | 23 |
| 14.0 | 27 | — |
| 24.0 | 6 | — |

B. A phase III open randomised comparative crossover study was conducted on 54 patients employing
(i) Controlled release dihydrocodeine tartrate (60 mg) tablets prepared as described in Example 5, and
(ii) Dihydrocodeine tartrate (30 mg) normal release tablets (DF118, Trade Mark),
in the control of moderate to severe pain in osteoarthritis.

On recruitment into the study, patients were randomly allocated to receive either controlled release or normal release tablets for 3 weeks. Patients were then "crossed over" to receive the alternative analgesic for a further 3 weeks. The starting dose in all cases was 120 mg dihydrocodeine tartrate per day, either one controlled release tablet taken twice a day or one normal release tablet taken four times a day.

At the end of the first week, the dose could be doubled to 240 mg dihydrocodeine tartrate per day, either two controlled release tablets taken twice a day or two normal release tablets taken four times a day, if pain control at the starting dose was unsatisfactory and side effects were not a problem.

Patients were crossed over to the second study medication on a mg. for mg. basis.

The patients were assessed for severity of pain (on a scale 0 (no pain) to 5 (severe pain)) both on entry to the study and at the end of each three week period.

Results of the pain assessment are given in Table 6.

TABLE 6

| | | Baseline | Normal Release DHC Tartrate | Controlled Release DHC Tartrate |
| --- | --- | --- | --- | --- |
| Pain scores | 0 | 0 | 1 | 1 |
| for | 1 | 5 | 4 | 9 |
| Completing | 2 | 26 | 26 | 23 |
| Patients | 3 | 15 | 7 | 5 |
| | 4 | 7 | 1 | 1 |
| | 5 | 1 | 0 | 0 |
| Non-Completing Patients | | 0 | 15 | 15 |
| Total | | 54 | 54 | 54 |

Using the Wilcoxon matched pairs signed rank test (see Non-parametric statistics for the behavioural sciences, S. Siegel, 1956), it was found that the difference between the categorical pain scores for baseline and controlled release tablets reached much greater significance ($p<0.01$) than the difference between the baseline and normal release tablets ($p<0.05$).

The patients were also assessed for severity of pain by the visual analogue score (VAS) method.

Results are given in Table 7.

TABLE 7

| | Baseline | Normal Release DHC Tartrate | Controlled Release DHC Tartrate |
| --- | --- | --- | --- |
| Patients Completing the study | 54 | 39 | 38 |
| VAS | 55.4 | 42.5 | 38.3 |

We claim:

1. A solid, controlled release, oral dosage form, the dosage form comprising an analgesically effective amount of dihydrocodeine or a salt thereof in a controlled release matrix of at least 2–20% by weight of at least one soluble hydroxyalkylcellulose and 8–40% by weight of at least one aliphatic alcohol of 12–36 carbon atoms wherein the dissolution rate in vitro of the dosage form, when measured by the USP Paddle Method at 100 rpm in 900 ml aqueous buffer (pH between 1.6 and 7.2) at 37° C. is between 25% and 60% (by wt) dihydrocodeine released after 1 hour, between 45% and 80% (by wt) dihydrocodeine released after 2 hours, between 60% and 90% (by wt) dihydrocodeine released after 3 hours and between 70% and 100% (by wt) dihydrocodeine released after 4 hours, the in vitro release rate being independent of pH between 1.6 and 7.2 and chosen such that the peak plasma level of dihydrocodeine obtained in vivo occurs between 2 and 4 hours after administration of the dosage form.

2. The dosage form according to claim 1 wherein the in vitro dissolution rate is between 25% and 50% (by weight) dihydrocodeine released after 1 hour, between 45% and 70% (by weight) dihydrocodeine released after 2 hours, between 60% and 80% (by weight) dihydrocodeine released after 3 hours and between 70% and 90% (by weight) dihydrocodeine released after 4 hours.

3. The dosage form according to claim 2 wherein the in vitro dissolution rate is between 30% and 50% (by weight) dihydrocodeine released after 1 hour, between 45% and 65% (by weight) dihydrocodeine released after 2 hours, between 60% and 75% (by weight) dihydrocodeine released after 3 hours and between 70% and 85% (by weight) dihydrocodeine released after 4 hours.

4. The dosage form according to claim 1 wherein the dosage form contains between 3% and 12% (by weight) of the at least one hydroxyalkylcellulose.

5. The dosage form according to claim 1 wherein an analgesically effective amount of a dihydrocodeine salt is between 30 and 180 mg of dihydrocodeine tartrate.

6. The dosage form according to claim 5 wherein an analgesically effective amount of a dihydrocodeine salt is between 60 and 120 mg of dihydrocodeine tartrate.

7. The dosage according to claim 1 wherein the controlled release matrix also includes at least one polyalkylene glycol.

8. The dosage form according to claim 7 wherein the at least one water soluble hydroxyalkylcellulose is a hydroxy $C_1$–$C_6$ alkyl cellulose.

9. The dosage form according to claim 1 wherein the at least one hydroxyalkyl cellulose is hydroxypropyl cellulose, hydroxypropylmethylcellulose or hydroxyethylcellulose.

10. The dosage form according to claim 9 wherein the at least one hydroxyalkylcellulose is hydroxyethylcellulose.

11. The dosage form according to claim 7 wherein the ratio of the at least one hydroxyalkylcellulose to the at least one aliphatic alcohol/polyalkylene glycol is between 1:2 and 1:4.

12. The dosage form according to claim 7 wherein the aliphatic alcohol is a $C_{14}$ to $C_{22}$ aliphatic alcohol.

13. The dosage form according to claim 12 wherein the aliphatic alcohol is lauryl alcohol, myristyl alcohol, stearyl alcohol, cetyl alcohol or cetostearyl alcohol.

14. The dosage form according to claim 13 wherein the aliphatic alcohol is cetyl alcohol or cetostearyl alcohol.

15. The dosage form according to claim 7 wherein the dosage form contains between 12% and 36% (by weight) of the at least one fatty alcohol or of the at least one fatty alcohol and the at least one polyalkylene glycol.

16. The dosage form according to claim 11 wherein the ratio is between 1:3 and 1:4.

17. A process for the preparation of a solid, controlled release, oral dosage form comprising incorporating an analgesically effective amount of dihydrocodeine or a salt thereof in as controlled release matrix of at least 2-20% by weight of at least one soluble hydroxyalkylcellulose and 8-40% by weight of at least one aliphatic alcohol of 12-36 carbon atoms wherein the dissolution rate in vitro of the dosage form, when measured by the USP Paddle Method of 100 rpm in 900 ml aqueous buffer (pH between 1.6 and 7.2) at 37° C. is between 25% and 60% (by weight) dihydrocodeine released after 1 hour, between 45% and 80% (by weight) dihydrocodeine released after 2 hours, between 60% and 90% (by weight) dihydrocodeine released after 3 hours and between 70% and 100% (by weight) dihydrocodeine released after 4 hours, the in vitro release rate being independent of pH between 1.6 and 7.2 and chosen such that the peak plasma level of dihydrocodeine obtained in vivo occurs between 2 and 4 hours after administration of the dosage form.

18. The process according to claim 17 comprising
(a) wet granulating at least one water soluble hydroxyalkylcellulose with dihydrocodeine or a dihydrocodeine salt to form granules,
(b) mixing the hydroxyalkylcellulose containing granules with at least one $C_{12}$–$C_{36}$ aliphatic alcohol, and
(c) compressing and shaping the granules.

19. The process according to claim 18 wherein the at least one water soluble hydroxyalkylcellulose and the dihydrocodeine or the dihydrocodeine salt are wet granulated with water, the weight ratio of the water to the dry weight of the at least one water soluble hydroxyalkylcellulose being between 1.5 to 1 and 5 to 1.

* * * * *